United States Patent [19]

Yokohari et al.

[11] Patent Number: 5,258,503
[45] Date of Patent: Nov. 2, 1993

[54] AUTOANTIBODY ADSORBENT AND APPARATUS FOR REMOVING AUTOANTIBODIES USING THE SAME

[75] Inventors: Ryuichi Yokohari, Matsudo; Shinichi Aotsuka, Shonan; Makiko Kinoshita, Tokyo; Takashi Funahashi, Kobe; Nobutaka Tani, Osaka, all of Japan

[73] Assignee: Kanegafuchi Kagaku Kogyo Kabushiki Kaisha, Osaka, Japan

[21] Appl. No.: 866,269

[22] Filed: Apr. 13, 1992

Related U.S. Application Data

[63] Continuation of Ser. No. 195,048, May 17, 1988, abandoned.

[30] Foreign Application Priority Data

Sep. 8, 1987 [JP] Japan .................. 62-224472
Sep. 8, 1987 [JP] Japan .................. 62-224473

[51] Int. Cl.$^5$ .................. A61N 5/00; B01D 39/00; C07K 3/18
[52] U.S. Cl. .................. 530/415; 210/502.1; 210/679; 436/824; 530/416; 604/5; 604/6
[58] Field of Search .................. 436/506, 508, 824; 530/415, 416; 604/5, 6; 210/502.1, 679

[56] References Cited

U.S. PATENT DOCUMENTS

| | | | |
|---|---|---|---|
| 4,103,685 | 8/1978 | Lupien et al. | 530/415 |
| 4,384,954 | 5/1983 | Nakashima et al. | 530/415 |
| 4,576,928 | 3/1986 | Tani et al. | 502/404 |
| 4,627,915 | 12/1986 | Kuroda | 210/195.2 |
| 4,637,994 | 1/1987 | Tani et al. | 502/404 |
| 4,654,420 | 3/1987 | Furuyoshi et al. | 210/502.1 |
| 4,666,831 | 5/1987 | Janoff et al. | 436/506 |
| 4,668,638 | 5/1987 | Janoff et al. | 436/507 |
| 4,725,355 | 2/1988 | Yamanoto et al. | 210/502.1 |

FOREIGN PATENT DOCUMENTS

| | | |
|---|---|---|
| 2543849 | 10/1984 | France . |
| 0170263 | 10/1982 | Japan . |
| 0186559 | 10/1984 | Japan . |
| 0189859 | 10/1984 | Japan . |

OTHER PUBLICATIONS

Herbert, et al. (Eds.), *Dictionary of Immunology*, Third Edition, Blackwell Scientific Publications, Oxford, 1985, p. 85.
*Affinity Chromatography Principles and Methods*, Publication of Pharmacia Fine Chemicals, 1974.

*Primary Examiner*—David Saunders
*Attorney, Agent, or Firm*—Armstrong, Westerman, Hattori, McLeland & Naughton

[57] ABSTRACT

An adsorbent for an autoantibody or immune complex produced by combining an autoantibody with its homologous antigen, which comprises a water-insoluble porous material and a compound having an anionic functional group immobilized onto said material, an apparatus for removing an autoantibody or immune complex thereof using the above-mentioned adsorbent and a method for removing an autoantibody or immune complex thereof from body fluid by passing body fluid through the above-mentioned removing apparatus. According to the present invention, the autoantibody or immune complex thereof can be selectively removed from body fluid without removing useful components in body fluid.

3 Claims, 2 Drawing Sheets

AUTOANTIBODY ADSORBENT AND APPARATUS FOR REMOVING AUTOANTIBODIES USING THE SAME

This application is a continuation of application Ser. No. 07/195,048 filed May 17, 1988 and now abandoned.

BACKGROUND OF THE INVENTION

The present invention relates to an adsorbent for removing or recovering autoantibodies or immune complexes produced by combining an autoantibody with their homologous antigens, from body fluid and to an apparatus for removing autoantibodies or immune complexes thereof using the same. And, the present invention relates to a method for removing autoantibodies or immune complexes thereof from body fluid by passing body fluid through the above-mentioned removing apparatus.

Autoimmune disease is a disease which is caused by being formed antibodies to the components of tissue in one's body (hereinafter referred to as "autoantibodies"), and as a typical autoimmune disease, there is exemplified systemic lupus erythematosus (SLE) or rheumatoid arthritis (RA).

In SLE, it is known that the immune system produces immunoglobulins capable of binding to the components of nucleus in cells, particularly, deoxyribonucleic acid (DNA), or that the immune system produces immunoglobulins capable of biding to phospholipid in cell membrane, and the antibodies against DNA (anti-DNA antibodies; anti-dsDNA) or the antibodies against phospholipid (anti-phospholipid antibody) appear in body fluid, which are closely related to the pathogenesis of SLE. Also, it is known that complexes are produced by combining autoantibodies with their homologous antigens (hereinafter referred to as "immune complexes"), and the immune complexes thereof with their homologous antigens appearing in body fluid are closely related to the pathogenesis of SLE.

On the other hand, in RA, it is known that the immune system produces immunoglobulins which form complexes with autologous Immunoglobulin G (IgG) as the reactant, and these immunoglobulins against IgG (rheumatoid factor, RF) appear in body fluid, which are also closely related to the pathogenesis of RA. Also complexes produced by combining RF with their homologous antigens, namely, immune complexes, appearing in body fluid, are closely related to the pathogenesis of RA.

The mechanism that the produced autoantibodies or immune complexes thereof with their homologous antigens lead to the above-mentioned diseases is not completely clarified. However, there are reported the mechanisms such that autoantibodies give damage to cells, and that autoantibodies form complexes with antigens and immune complexes are deposited in tissue, which results in disorder in the tissues.

In SLE, it is known that the produced anti-DNA antibodies are combined with DNA originated in cells, which is outflowed into blood, to form an immune complex, and immune complexes are deposited around blood vessels or in the glomerulus, which results in angiitis or lupus nephritis. Also, it is known that the produced anti-phospholipid antibodies are combined with phospholipid in cell membrane, outflowed into blood, to form immune complexes, and immune complexes are deposited around blood vessels or in the glomerulus, which results in thrombosis or thrombocytopenia. Actually, renal insufficiency is the main cause of death in SLE.

Also with respect to RF, it is known that the produced RF is combined with an IgG in blood to form an immune complex, and immune complexes are deposited around blood vessels, which results in angiitis, or immune complexes are deposited on synovial membranes, which results in arthritis.

As aforementioned, various symptoms of diseases are caused by the produced anti-DNA antibodies or immune complexes thereof with DNA, the produced anti-phospholipid antibodies or immune complexes thereof with phospholipid, or the produced RF or immune complexes thereof with IgG in blood, and the like. Accordingly, it is very important to control autoantibodies such as the anti-DNA antibody, the anti-phospholipid antibody and RF in the treatments of the autoimmune diseases such as SLE and RA.

Hitherto, there have been widely used in the treatment of the autoimmune diseases such as SLE and RA, steroid, an immunosuppressor, immuno modulator, an anti-inflammatory agent, and the like, for the purpose of controlling the production of autoantibodies such as the anti-DNA antibody, the anti-phospholipid antibody, and RF and immune complexes thereof with their homologous antigens. Among them, corticosteroids are most popularly used. For example, there is often conducted a treatment in which an extremely large dose of oral corticosteroids is administered intermittently to the patient in a short term, what is called pulse therapy. However, steroids are apt to produce side effects by even its small amount of administration. Therefore, more serious side effects cannot be avoided when the administration of steroid is administered in an extremely large amount and in a short term. Further, since the above-mentioned agents are rather frequently used in a long-term administration, side effects are produced more easily. Furthermore, there occurs very often a case that the dose of the agents must be increased more and more due to drug resistance. As the result, it become impossible to use these agents or to exhibit the effects of the agents satisfactorily, depending on the patient's condition. Particularly, although it is most necessary to control anti-DNA antibodies, anti-phospholipid antibodies and immune complexes thereof with their homologous antigens during the period that a patient of active SLE, there happen quite often cases where pulse therapy or the effective treatment using the agents such as the immunosuppressor cannot be adopted because of the above-mentioned reasons.

Also, in the treatment of RA, it is known that steroid shows a dramatic effect for controlling the production of RF and immune complexes thereof. However, some patients suffering from RA for several years suddenly show symptoms of malignant rheumatoid arthritis, which is more malignant than RA, accompanied by a rise in the body temperature, and, most of them had been administered steroid in the past. Accordingly, there is still a strong suspicion that steroids act at least partially in triggering the onset of malignant rheumatoid arthritis.

Then, as an another treatment besides the drug therapy, there is attempted an extracorporeal circulation treatment, in which autoantibodies existing in body fluid such as the anti-DNA antibody, the anti-phospholipid antibody or RF, and immune complexes thereof with their homologous antigens are directly removed. It is the most simple method to replace the partient's plasma containing autoantibodies such as the anti-DNA antibody, the anti-phospholipid antibody and RF, and immune complexes thereof with their homologous antigens, with plasma obtained from a healthy body, what is called plasma exchange. By means of the plasma exchange, autoantibodies such as the anti-DNA antibody, the anti-phospholipid antibody and RF, and immune complexes thereof are remarkably decreased, and the symptoms are alleviated. However, this treatment is costly because a large quantity of plasma obtained from healthy bodies is required, in addition, it involves the danger that the transfused blood is infected with serum hepatitis or HIV during the treatment. Accordingly, the plasma exchange is not widely employed for the present.

In the plasma exchange, plasma of a patient including all components of the plasma is replaced with plasma obtained from healthy bodies. On the other hand, there is developed a method for the separation of blood plasma component using a membrane in order to selectively remove pathogenic substances, i.e. autoantibodies such as the anti-DNA antibody, the anti-phospholipid antibody and RF, and immune complexes thereof with their homologous antigens. In the method, based on the volume of molecules, high molecular weight components including the pathogenic substances are removed from the plasma using a membrane, and the plasma having low molecular components including the main protein, i.e. albumin is returned into the patient's body. However, autoantibodies are composed of IgG (immunoglobulin G) having a molecular weight of about $1.6 \times 10^5$ or IgM (immunoglobulin M) having a molecular weight of about $9 \times 10^5$, besides, immune complexes produced by combining autoantibody with its homologous antigen has a wide range of molecular weight. Therefore, not all of the autoantibodies and the immune complexes cannot be separated from albumin having a molecular weight of about 60,000, or normal IgG and IgM according to the volume of the molecule. As the result, there occur problems such that a large amount of albumin is also removed when autoantibodies and immune complexes are removed, and further, all proteins having a molecular weight equal to, or larger than that of the pathogenic substances are removed during the separation.

From the above-mentioned problems, there has been desired a method for more selectively removing the pathogenic substances, i.e. autoantibodies such as the anti-DNA antibody, the anti-phospholipid antibody and RF, and immune complexes thereof with their homologous antigens, and yet, the useful components are not removed from the body fluid.

It is an object of the present invention to provide a means for selectively removing only autoantibodies such as the anti-DNA antibody, the anti-phospholipid antibody and RF, and immune complexes thereof with their homologous antigens from body fluid without losing the useful components in the body fluid.

This and other objects of the present invention will become apparent from the description hereinafter.

SUMMARY OF THE INVENTION

There has now been found an adsorbent capable of selectively adsorbing autoantibodies such as the anti-DNA antibody, the anti-phospholipid antibody and RF, and immune complexes thereof with their homologous antigens, without losing the useful components in body fluid.

That is, in accordance with the present invention, there is provided an adsorbent for autoantibodies or immune complexes produced by combining an autoantibody with its homologous antigen which comprises a water-insoluble porous material and a compound having an anionic functional group immobilized onto the material.

Also in accordance with the present invention, there is provided an apparatus for removing autoantibodies or immune complexes produced by combining an autoantibody with its homologous antigen which comprises a container having a fluid inlet and a fluid outlet, at least one filter through which a fluid and components included in the fluid can pass while the above-mentioned adsorbent cannot pass at the fluid outlet side, and the adsorbent packed in the container.

Further, in accordance with the present invention, there is provided a method for removing autoantibodies or immune complexes produced by combining an autoantibody with its homologous antigen from body fluid which comprises passing body fluid containing autoantibodies or immune complexes produced by combining an autoantibody with its homologous antigen through the above-mentioned removing apparatus.

The adsorbent, apparatus and method of the present invention are particularly suitable for removing or recovering the anti-DNA antibody, the anti-phospholipid antibody and RF, and immune complexes thereof with their homologous antigens from body fluid.

DETAILED DESCRIPTION

In the present invention, the term "body fluid" is blood, plasma, serum, ascites, lymph liquid, synovia in articular cavity, fractions thereof or any fluid components originated in a living body.

It is preferable for a water-insoluble porous material used in the present invention to have continuous large size pores. That is to say, since autoantibodies such as the anti-DNA antibody, the anti-phospholipid antibody or RF is a macromolecule having a molecular weight of $1.6 \times 10^5$ to $9 \times 10^5$, in addition immune complexes produced by combining the autoantibody with its homologous antigen is supposed to include a macromolecule having a molecular weight of about $1.0 \times 10^6$, it is required that the autoantibody and the immune complex thereof can easily enter into the porous material to be efficiently adsorbed.

For measuring the pore size, there are various kinds of methods. Though mercury porosimetry is most frequently employed, it is difficult to apply to a hydrophilic porous material. An exclusion limit is usually adopted as a measure of the pore size of both a hydrophilic and hydrophobic porous material.

The term "exclusion limit" in the present invention means, as described in the literature such as "Jikken Kosoku Ekitai Chromatography (Experimental High Performance Liquid Chromatography)", Hiroyuki Hatano and Toshihiko Hanai, published by Kabushiki Kaisha Kagaku Dojin, the minimum molecular weight of the molecule which cannot permeate into a pore, i.e. which is excluded, in a gel permeation chromatography. It is known that a value of an exclusion limit varies depending on the kind of the compound employed, among which exclusion limit values with such molecules as globular proteins, dextran and polyethylene glycol have been fully investigated. In the present invention, a value of an exclusion limit obtained from the globular proteins including virus, which are regarded as the most similar compounds to autoantibodies such as the anti-DNA antibody, the anti-phospholipid antibody or RF, and immune complexes thereof with its homologous antigen, is suitably employed.

As the result of an investigation, using various water-insoluble porous materials having various values of an exclusion limit, it is unexpectedly shown that a material having an exclusion limit value of about $1 \times 10^5$, which is smaller than the molecular weight of autoantibody such as the anti-DNA antibody, the anti-phospholipid antibody or RF, and immune complexes thereof with its homologous antigen, can adsorb these autoantibodies and the immune complexes thereof with their homologous antigens to some extent and that a material having a larger pore size does not always exhibit an increased capacity of adsorption but, conversely, it is observed that an adsorption capacity of such material decreases or proteins other than the autoantibodies and the immune complexes thereof with their homologous antigens are likely to be adsorbed, which means there exist an optimum range of a pore size. That is, it is found that a water-insoluble porous material having an exclusion limit of less than $1 \times 10^5$ can hardly adsorb the autoantibodies and the immune complexes thereof with their homologous antigens, and is not suited for practical use, whereas a water-insoluble porous material having an exclusion limit of from $1 \times 10^5$ to $1.5 \times 10^5$, which is close on the molecular weight of autoantibodies and immune complexes thereof with their homologous antigens, can adsorb the autoantibodies and the immune complexes thereof with their homologous antigen to some extent. Subsequently, it is observed that an amount of adsorbed autoantibodies and immune complexes thereof with their homologous antigens increases as an exclusion limit increases, and then reaches maximum, and it extremely decreases when an exclusion limit is over $6 \times 10^7$ because of too small surface area of the adsorbent. In addition, the adsorption of components of body fluid other than the desired autoantibodies such as the anti-DNA antibody the anti-phospholipid antibody and RF, and immune complexes thereof with their homologous antigens, namely, non-specific adsorption is increased. Accordingly, the selectivity is remarkably lowered.

Therefore, the exclusion limit of water-insoluble porous material used in the present invention is preferably from $1 \times 10^5$ to $6 \times 10^7$, more preferably from $4 \times 10^5$ to $2 \times 10^7$ from the viewpoint of the capacity for selectively adsorbing the autoantibodies and the immune complexes thereof with their homologous antigens.

With respect to a porous structure of a water-insoluble porous material used in the present invention, a structure uniformly having pores at any part of the material is more preferable than a structure having pores only on the surface of the material. And it is preferred that a porosity of the material used in the present invention is not less than 20% in consideration of the capacity for the adsorption. A shape of a water-insoluble porous material used in the present invention can be optionally selected from shapes such as particle, sphere, fiber, sheet and hollow fiber. When a water-insoluble porous material with a shape of particle is used, the particle size is preferably from 1 to 5,000 $\mu$m. When the particle size is less than 1 $\mu$m, the pressure drop becomes large, and when the particle size is over 5,000, the capacity becomes small.

A water-insoluble porous material used in the present invention can be organic or inorganic. It is desirable to use the material with little non-specific adsorption. A hydrophilic water-insoluble porous material is preferable rather than a hydrophobic one because the non-specific adsorption scarcely occurs. Also, a water-insoluble porous material comprising a compound having hydroxyl group in its molecule is more preferable.

Typical examples of water-insoluble porous material used in the present invention are, for example, soft porous materials such as agarose, dextran and polyacrylamide, inorganic porous materials such as porous glass and porous silica gel, synthetic high molecular compounds such as polymethyl methacrylate, polyvinyl alcohol and styrene-divinylbenzene copolymer, porous polymer hard gels made of a natural high molecular compound such as cellulose, and the like. However, the present invention is not limited thereto.

When the adsorbent of the present invention is adopted to the extracorporeal circulation treatment, it is necessary to flow a fluid having a high viscosity such as blood or plasma at a high flow rate. Therefore, it is desirable to use the adsorbent having a sufficient mechanical strength, i.e. hard adsorbent, so as to prevent consolidation of the adsorbents in a column.

The term "hard" in the present invention means, as shown in the Reference Example herein below, that the relation between a pressure drop and a flow rate determined by passing an aqueous fluid through a cylindrical column uniformly filled with the water-insoluble porous material keeps a linear relationship until the pressure drop is increased to 0.3 kg/cm$^2$, which is the minimum required mechanical strength of the adsorbent for incorporating the column into an extracorporeal circulation circuit.

In the present invention, any anionic functional groups can be used so long as the functional groups are charged with negative electricity in pH value around neutrality. Typical examples of the anionic functional group are, for instance, carboxyl group, sulfonic acid group, sulfonate group, sulfate group, silanol group, phosphate group, phenolic hydroxyl group, thiol group and the like, but the groups are not limited thereto.

Among them, carboxyl group, sulfonic acid group, sulfate group, phosphate group and thiol group are preferred in that they have excellent affinity to autoantibodies such as the anti-DNA antibody, the anti-lipidal antibody and RF and immune complexes thereof with their homologous antigens.

As the compound having the anionic functional group, which is immobilized onto the water-insoluble porous material, there can be used both a monoanionic compound which has an anionic functional group in its molecule and a polyanionic compound which has more than one anionic functional groups. The polyanionic compound is preferable because it has an excellent affinity to autoantibodies such as the anti-DNA antibody, the anti-phospholipid antibody and RF, and immune complexes thereof with their homologous antigens, and a lot of the anionic functional groups are easily introduced into a unit of the porous meterial. The polyanionic compound having a molecular weight of not less than 1,000 is especially preferable from the point of the affinity and the quantity of the anionic functional groups introduced. The anionic functional groups in a polyanionic compound may be the same or different.

Typical examples of the polyanionic compound are, for instance, a synthetic polyanionic compound such as polyacrylic acid, polyvinyl sulfonic acid, oblyvinyl phosphoric acid, polystyrenesulfonic acid, polystyrenephosphoric acid, polyglutamic acid, polyaspartic acid, polymethacrylic acid, polyphosphoric acid or a styrenemaleic acid copolymer; a polysaccharide having anionic functional groups such as heparin, heparan sulfate, dextran sulfate, chondroitin, chondroitin sulfate or phosphomannan; a nucleic acid such as polyinosinic acid, polyadenylic acid, polyguanylic acid, polycytidylic acid or polyuridylic acid; and the like. The polyanionic compounds are not limited thereto.

In the present invention, both of the same or different kinds of the compounds having the anionic functional groups can be immobilized onto the water-insoluble porous material.

There are various methods for introducing the anionic functional groups into the adsorbent and any methods can be applied to the invention. As methods for introducing the anionic functional group into the adsorbent, there are exemplified, for instance, (1) a method in which monomers or crosslinking gents having the anionic functional group or a group capable of easily converting into the anionic functional group are polymerized to form the adsorbent, (2) a method in which the anionic functional group-containing compound is immobilized on a water-insoluble porous material, (3) a method in which a compound capable of forming the anionic functional group is directly reacted with a water-insoluble porous material, and the like.

Of course, the anionic functional group-containing compound having the anionic functional group in itself such as glass, silica and alumina may be used as the adsorbent.

In the method (1), examples of the monomers or crosslinking agents are, for instance, acrylic acid, acrylic acid ester, methacrylic acid, methacrylic acid ester, styrenesulfonic acid, and the like, but the monomers or crosslinking agents are not limitedthereto.

In the process (2), the anionic functional group-containing compound is immobilized onto the water-insoluble porous material by any methods, for example, physical adsorption, ionic bond, covalent bond, and the like. In case of using the adsorbent for a medical treatment, it is important that the anionic functional groups are not eliminated from the adsorbent during the sterilization or the treatment. Accordingly, it is desirable, for the above-mentioned purpose, to use the adsorbent obtained by the method capable of forming a covalent bond which is able to firmly immobilized the functional group onto the porous material.

When the compound having an anionic functional group is immobilized onto the water-insoluble porous material by a covalent bond, it is more preferable to use the compound having a functional group utilizable for the immobilization onto the porous material, besides the anionic functional group.

Examples of the functional group utilizable for the immobilization are, for instance, amino group, amide group, carboxyl group, acid anhydride group, succinylimide, hydroxyl group, thiol group, aldehyde group, halogen group, epoxy group, silanol group, and the like. The functional groups are not limited thereto.

There exist a lot of compounds which have both the anionic functional groups and the above-mentioned functional groups utilizable for the immobilization. As these compounds, there is exemplified taurine, sulfanilic acid, 2-aminoethyl hydrogensulfate, terephthalic acid, glycine, phosphoryl ethanolamine, glucose-6-phosphate or ethanedithiol, mentioned in Examples.

As compounds having sulfate group among the anionic functional group-containing compound, there are exemplified, for instance, sulfuric acid esters of hydroxyl group-containing compounds such as alcohol, saccharides and glycol. Among them, there is preferred sulfuric acid esters having a functional group which can be utilized for the immobilization onto the water-insoluble porous gel in addition to sulfate group. Among the above sulfuric acid esters, partially sulfated polyhydric alcohols, and particularly sulfated saccharide are preferable, since the sulfuric acid esters hot only have both sulfate group and the functional group necessary for the immobilization but also are high in the biocompatibility and the activity. A sulfated polysaccharide is especially preferable since it can be easily immobilized onto the water-insoluble porous material.

As the representative example of the method (3), there are, for instance, a method in which sulfate group is introduced into a water-insoluble porous material having hydroxyl group, and the like. In such a case, sulfate group can be directly introduced into the adsorbent by reacting a reagent such as chlorosulfonic acid or concentrated sulfuric acid with the water-insoluble porous material having hydroxyl group.

It is preferable that the amount of the introduced anionic functional group is from 0.01 $\mu$mol to 10 mmol per 1 ml of the adsorbent. When the amount is less than 0.01 $\mu$mol, a sufficient adsorbing capacity cannot be obtained. When the amount is more than 10 mmol, non-specific adsorption increases, which make the adsorbent unsuitable for a practical usage. It is more preferable that the amount of the introduced anonic functional group is from 1 $\mu$mol to 100 $\mu$mol per 1 ml of the adsorbent.

There are various methods for removing autoantibodies such as the anti-DNA antibody, the anti-phospholipid antibody and RF or immune complexes produced by combining an autoantibody with its homologous antigen from body fluid by using the adsorbent of the present invention, and any methods can be adopted in the invention. Among them, the following method is simple and easy. That is, body fluid containing autoantibodies or immune complexes produced by combining an autoantibody with its homologous antigen is passed through an apparatus for removing autoantibodies or immune complexes produced by combining an autoantibody with its homologous antigen, which comprises a container having a fluid inlet and a fluid outlet, at least one filter through which a fluid and components included in the fluid can pass while an adsorbent for autoantibodies or immune complexes produced by combining an autoantibody with its homologous antigen, which comprises a water-insoluble porous material and a compound having an anionic functional group immobilized onto the carrier, cannot pass at the fluid outlet side, and the adsorbent packed in the container.

Figure 2:
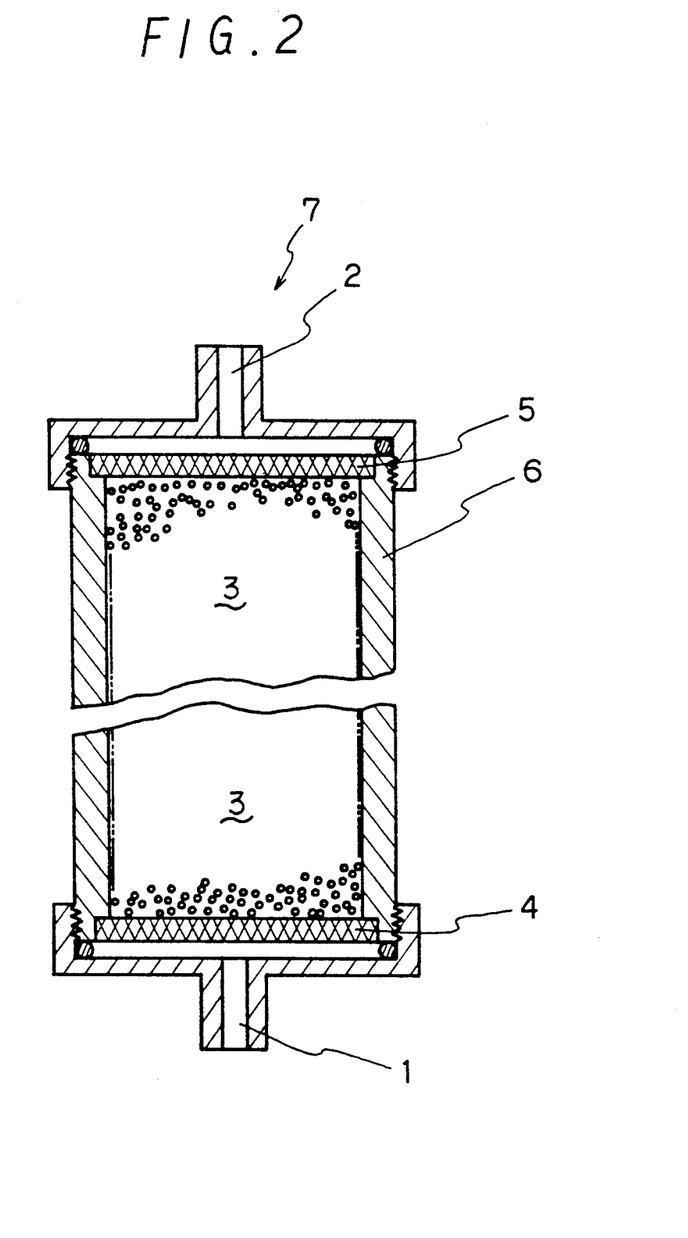
FIG. 2 is a schematic longitudinal sectional view of an example of apparatus for removing autoantibodies or immune complexes produced by combining autoantibodies with their homologous antigens.

A schematic longitudinal sectional view of the example of the apparatus for removing autoantibodies of the present invention is shown in FIG. 2.

In FIG. 2, 1 and 2 are a fluid inlet and a fluid outlet respectively, 3 is the adsorbent of the present invention, 4 and 5 are filters or mesh which the fluid and components thereof can pass through while the adsorbent can not pass through, 6 is a column, and 7 is a container. The filter 4 of the fluid inlet side may be excepted.

The present invention is more specifically described and explained by the following Reference Example, Preparation Examples and Examples in which all % are by weight otherwise noted. It is to be understood that the present invention is not limited to the Reference Example, Preparation Examples and Examples and various changes and modifications can be made without departing from the scope and spirit of the present invention.

REFERENCE EXAMPLE

A relation between a flow rate and a pressure drop P was determined by passing water by means of a peristartic pump through cylindrical glass columns equipped at both ends with filters having a pore size of 15 μm (inner diameter: 9 mm, column length: 150mm), in which an agarose gel (Biogel A5m made by Biorad Co., particle size: 50 to 100 mesh), a gel made of a synthetic polymer (Toyopearl HW 65 made by Toyo Soda Manufacturing Co., Ltd., particle size: 50 to 100 μm) and a porous cellulose gel (Cellulofine GC 700m made by Chisso Corporation, particle size: 45 to 100 μm) were packed respectively. The results are shown in FIG. 1.

Figure 1:
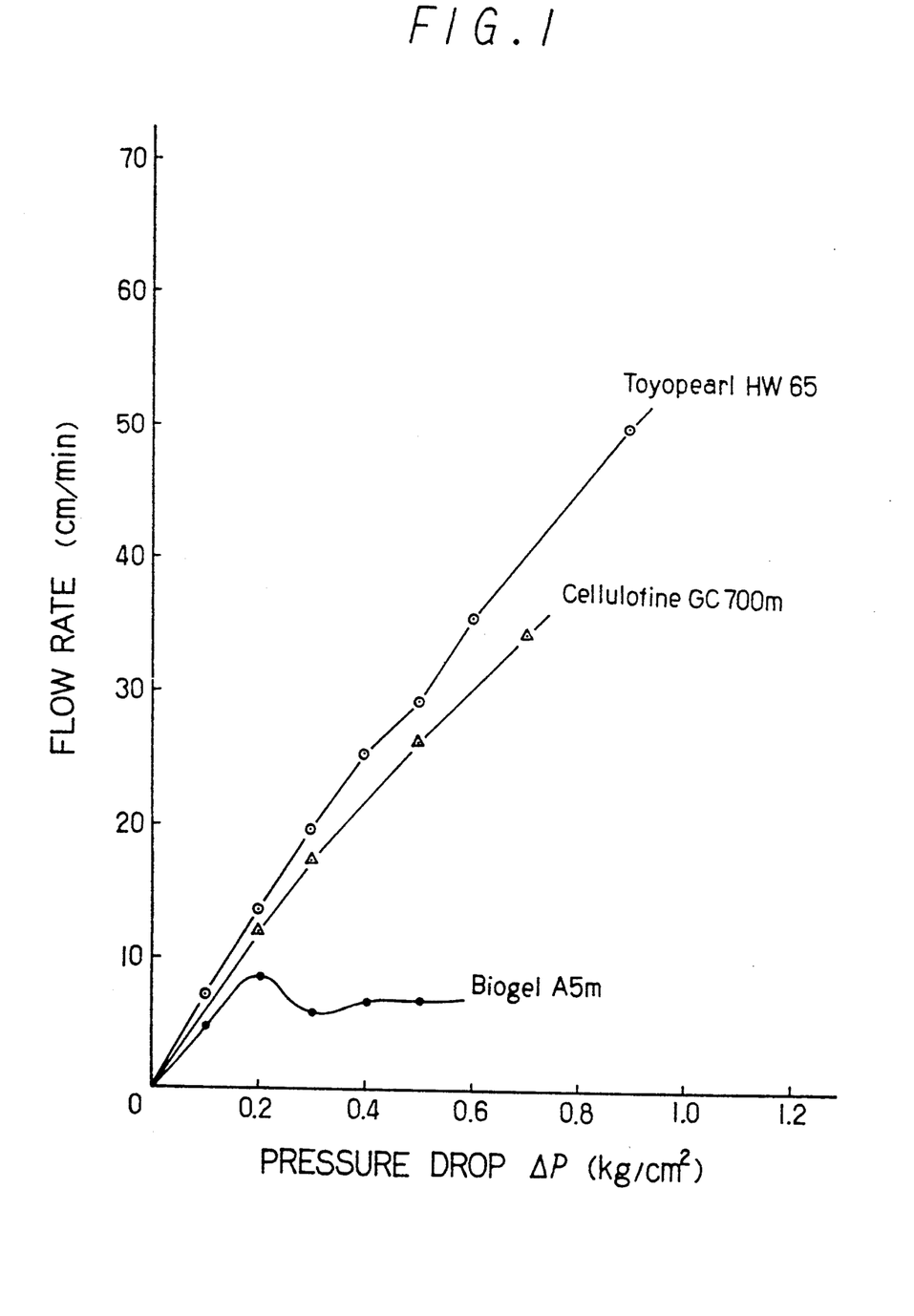
FIG. 1 is a graph showing a relation between a flow rate and a pressure drop $\Delta p$ obtained in Reference Example, mentioned later.

As shown in FIG. 1, an increase of a flow rate is nearly proportional to that of a pressure drop in case of hard gels, i.e. Toyopearl and Cellulofine, whereas in case of soft gel, i.e. the agarose gel, consolidation occurs and a flow rate does not increase even if a pressure drop increases.

PREPARATION EXAMPLE 1

To 100 ml of a porous cellulose gel (CK gel A3 made by Chisso Corporation, exclusion limit of globular proteins: $5 \times 10^7$, particle size: 45 to 105 μm) were added 40 g of 20% NaOH, 120 g of heptane and 10 drops (0.5 ml) of the nonionic surfactant TWEEN 20 (a commercially available polyoxyethylene sorbitol fatty acid ester made by Kao Atlas Kabushiki Kaisha). After stirring for 2 hours at 40° C., there was added 50 g of epichlorohydrine. Further, after the stirring was continued for 2 hours at 40° C., the gel was filtered off from the reaction mixture and was washed with water to give an epoxidated cellulose gel (hereinafter referred to as "epoxidated gel").

PREPARATION EXAMPLE 1a

To 100 ml of CK gel A3 were added 60 ml of water and 80 ml of 2M NaOH and the mixture was stirred at 45° C. for 1 hour, to which 25 ml of epichlorohydrine was added, and then the mixture was stirred at 45° C. for 2 hours. After completing the reaction, the gel was filtered off from the reaction mixture and was washed with water to give an epoxidated gel.

EXAMPLE 1

To 5 ml of the epoxidated gel obtained in Preparation Example 1 was added a solution prepared by dissolving 0.17 g of sulfanilic acid in 10 ml of water and adjusting the pH value to 9.9, and the mixture was shaken for 24 hours at room temparature. The unreacted epoxy group in the gel was blocked by adding 0.5% aqueous solution of monoethanolamine to the gel and shaking to give a cellulose gel with immobilized sulfanilic acid. The amount of the introduced anionic functional group derived from the immobilized sulfanilic acid was 6.5 μmol to 1 ml of the adsorbent.

EXAMPLE 1a

To 10 ml of the epoxidated gel obtained in Preparation Example 1a was added a solution of 0.14 g of sulfanilic acid in 7.5 ml of water. Further, 2M NaOH was added thereto to adjust the pH value of the mixture to 10, and then the mixture was allowed to stand at 45° C. for 20 hours. After the reaction was completed, the gel was filtered off from the reaction mixture to give a cellulose gel with immobilized sulfanilic acid. The amount of the introduced anionic functional group derived from the immobilized sulfanilic acid was 10 μmol to 1 ml of the adsorbent.

EXAMPLE 2

To 5 ml of the epoxidated gel obtained in Preparation Example 1 was added a solution prepared by dissolving 0.1 g of phosphoryl ethanolamine in 10 ml of water and adjusting the pH value to 9.6, and the mixture was shaken for 4 hours at 40° C. The unreacted epoxy group in the gel was blocked by adding 0.5% aqueous solution of monoethanolamine to the gel and shaking to give a cellulose gel with immobilized phosphoryl ethanolamine. The amount of the introduced anionic functional group derived from the immobilized phosphoryl ethanolamine was 4 μmol to 1 ml of the adsorbent.

EXAMPLE 2a

The procedure of Example 1a was repeated except that 0.11 g of phosphoryl ethanolamine was used instead of sulfanilic acid to give a cellulose gel with immobilized phosphoryl ethanolamine. The amount of the introduced anionic functional group derived from the immobilized phosphoryl ethanolamine was 10 μmol to 1 ml of the adsorbent.

EXAMPLE 3

To 5 ml of the epoxidated gel obtained in Preparation Example 1 were added 4 g of sodium dextran sulfate (molecular weight: about 5,000, sulfur content: 15%) and 5 ml of water, the pH of the mixture was adjusted to pH 9 and the mixture was shaken at 45° C. for 16 hours. Then, the gel was filtered off from the reaction mixture and was washed, first, with 2M aqueous solution of sodium chloride, and secondly with 0.5M aqueous solution of sodium chloride, and finally with water. The unreacted epoxy group in the gel was blocked by adding 0.5% aqueous solution of monoethanolamine to the gel and shaking to give a cellulose gel with immobilized sodium dextran sulfate. The amount of the introduced anionic functional group derived from immobilized dextran sulfate was 10 μmol to 1 ml of the adsorbent.

EXAMPLE 3a

To 10 ml of the epoxidated gel obtained in Preparation Example 1a were added 5 g of sodium dextran sulfate (molecular weight: about 5,000, sulfur content: 18%) and 8 ml of water, to which 2M NaOH was further added to adjust the pH value of the mixture to 10, and then the mixture was allowed to stand at 45° C. for 17 hours. After the reaction was completed, the gel was filtered off from the reaction mixture and washed with water. The unreacted epoxy group in the gel was blocked by adding 0.5% aqueous solution of monoethanolamine to the gel and allowing to stand at room temperature for 20 hours. Then, the gel was filtered off from the resultant mixture and washed with water to give a cellulose gel with immobilized sodium dextran sulfate. The amount of the introduced anionic functional group derived from dextran sulfate was 29 $\mu$mol to 1 ml of the adsorbent.

EXAMPLE 4

To 5 ml of the epoxidated gel obtained in Preparation Example 1 was added a solution prepared by dissolving 0.22 g of glycine in 10 ml of water and adjusting the pH value to 9.8, and the mixture was shaken for 24 hours at room temperature. The unreacted epoxy group in the gel was blocked by adding 0.5% aqeous solution of monoethanolamine to the gel and shaking to give a cellulose gel with immobilized glycine. The amount of the introduced anionic functional group derived from the immobilized glycine was 9 $\mu$mol to 1 ml of the adsorbent.

EXAMPLE 5

To 5 ml of the epoxidated gel obtained in Preparation Example 1 was added a solution prepared by dissolving 0.37 g of taurine in 10 ml of water and adjusting the pH value to 9.0, and the mixture was shaken for 24 hours at room temperature. The unreacted epoxy group in the gel was blocked by adding 0.5% aqueous solution of monoethanolamine to the gel and shaking to give a cellulose gel with immobilized taurine. The amount of the introduced anionic functional group derived from the immobilized taurine was 5 $\mu$mol to 1 ml of the adsorbent.

EXAMPLE 5a

The procedure of Example 1a was repeated except that 0.11 g of 2-aminoethyl hydrogensulfate was used instead of sulfanilic acid to give a cellulose gel with immobilized 2-aminoethyl hydrogensulfate. The amount of the introduced anionic functional group derived from the immobilized 2-aminoethyl hydrogensulfate was 10 $\mu$mol to 1 ml of the adsorbent.

EXAMPLE 5b

The procedure of Example 1a was repeated except that 0.08 g of 1,2-ethanedithiol was used instead of sulfanilic acid to give a cellulose gel with immobilized 1,2-ethanedithiol. The amount of the introduced anionic functional group derived from the immobilized 1,2-ethanedithiol was 10 $\mu$mol to 1 ml of the adsorbent.

PREPARATION EXAMPLE 2

To 40 ml of the epoxidated gel obtained in Preparation Example 1 was added a solution of 0.5 g of ethylenediamine in 30 ml of water, and the mixture was allowed to stand at 45° C. for 20 hours. After the reaction was completed, the gel was filtered off from the reaction mixture and washed with water to give a cellulose gel on which an amino group was introduced (hereinafter referred to as "aminated gel").

EXAMPLE 5c

To 10 ml of the aminated gel obtained in Preparation Example 2 were added, first 10 ml of water, next 1 g of barium glucose-6-phosphate, to which 0.5 ml of 2M NaOH was further added and the mixture was maintained at 45° C. for 1 hour. After 0.1 g of NaBH$_4$ was added thereto, the mixture was allowed to stand at room temperature for 24 hours. After the reaction was completed, the gel was filtered off from the reaction mixture and washed with water to give a cellulose gel with immobilized glucose-6-phosphate. The amount of the introduced anionic functional group derived from the immobilized glucose-6-phosphate was 10 $\mu$mol to 1 ml of the adsorbent.

EXAMPLE 5d

There was prepared a suspension of 10 ml of the aminated gel obtained in Preparation Example 2 in N,N-dimethylformamide (DMF) with the total volume of 18 ml. After 0.27 g of terephthalic acid was dissolved in the suspension, 1 g of a condensing reagent (N,N'-dicyclohexylcarbodiimide) was added thereto, which was stirred at room temperature for 24 hours. After the reaction was completed, the gel was filtered off from the reaction mixture and washed, first with DMF, secondly with ethanol, and finally with water to give a cellulose gel with immobilized terephthalic acid. The amount of the introduced anionic functional group derived from the immobilized terephthalic acid was 10 $\mu$mol to 1 ml of the adsorbent.

EXAMPLE 5e

To 10 ml of the aminated gel obtained in Preparation Example 2 were added 5 g of the sodium dextran sulfate used in Example 3a and 8 ml of water. After 0.5 ml of 2M NaOH was added thereto, the mixture was maintained at 45° C. for 1 hour, to which 0.1 g of NaBH$_4$ was added and the mixture was allowed to stand at room temperature for 24 hours. After the reaction was completed, the gel was filtered off from the reaction mixture and washed with water to give a cellulose gel with immobilized sodium dextran sulfate. The amount of the introduced anionic functional group derived from the immobilized dextran sulfate was 39 $\mu$mol to 1 ml of the adsorbent.

PREPARATION EXAMPLE 3

There was prepared a suspension of 40 ml of CK gel A3 in heptane with the total volume of 70 ml. To the suspension were added 10 ml of 20% NaOH and 40 drops (2.0 ml) of the nonionic surfactant TWEEN 20, and the mixture was shaken at 40° C. for 30 minutes. Then, 10 ml of epichlorohydrine was added thereto and the mixture was shaken at 40° C. for 6 hours. After the reaction completed, the gel was filtered off from the reaction mixture and washed with ethanol first, and then with water to give an epoxidated gel.

EXAMPLE 5f

The procedure of Example 3a was repeated except that 10 ml of the epoxidated gel obtained in Preparation Example 3 was used instead of the epoxidated gel obtained in Preparation Example 1a to give a cellulose gel with immobilized sodium dextran sulfate. The amount of the introduced anionic functional group derived from immobilized dextran sulfate was 36 $\mu$mol to 1 ml of the adsorbent.

EXAMPLE 5g

To 10 ml of the epoxidated gel obtained in Preparation Example 3 was added a solution of 1 g of polyacrylic acid having an amino group at one side of the polymer ends (molecular weight: about 1,000) in 5 ml of water, to which 1 ml of 2M NaOH was added, and then the mixture was allowed to stand at room temperature for 48 hours. After the reaction was completed, the gel was filtered off from the reaction mixture and washed with water to give a cellulose gel with immobilized polyacrylic acid. The amount of the introduced anionic functional group derived from the immobilized polyacrylic acid was 560 $\mu$mol to 1 ml of the adsorbent.

The polyacrylic acid having an amino group at one side of the polymer ends was obtained by low polymerization reaction of acrylic acid using 2-aminoethanethiol as a chain transfer agent and a,a'-azobisisobutyronitrile (AIBN) as an initiator (mentioned in Nippon Kagaku Kaishi, 1, 88 to 92 (1977), "2-Hydroxyethyl methacrylate-styrene kei ABA gata bulokku kyojugo no gosei oyobi sono kozo to nure" by Mitsuo Okano, and the like).

EXAMPLE 5h

The procedure of Example 5g was repeated except that 1 g of polyacrylic acid having an amino group at one side of the polymer ends (molecular weight: about 10,000) was used instead of the polyacrylic acid having an amino group at one side of the polymer ends (molecular weight: about 1,000) to give a cellulose gel with immobilized polyacrylic acid. The amount of the introduced anionic functional group derived from the immobilized polyacrylic acid was 5.6 mmol to 1 ml of the adsorbent.

The polyacrylic acid having an amino group at one side of the polymer ends was obtained by a similar process to the processes mentioned in Example 5g.

PREPARATION EXAMPLE 4

The procedure of preparation Example 2 was repeated except that a solution of 0.12 g of ethylenediamine in 6 ml of water was added to 10 ml of the epoxidated gel obtained in Preparation Example 3 to give an aminated gel.

EXAMPLE 5i

The procedure of Example 5e was repeated except that 10 ml of the aminated gel obtained in Preparation Example 4 was used instead of the aminated gel obtained in Preparation Example 2 to give a cellulose gel with immobilized sodium dextran sulfate. The amount of the introduced anionic functional group derived from the immobilized dextran sulfate was 76 $\mu$mol to 1 ml of the adsorbent.

EXAMPLE 6

Ten ml of CK gel A3 was washed with water and filtered with suction, to which 6 ml of dimethyl sulfoxide, 2.6 ml of 2N NaOH and 1.5 ml of epichlorohydrine were added, and the mixture was stirred at 40° C. for 2 hours. After the reaction was completed, the gel was filtered off from the reaction mixture and was washed with water to give a cellulose gel on which an epoxy group was introduced.

To the obtained cellulose gel was added 6 ml of concentrated aqueous ammonia and the mixture was reacted at 40° C. for 2 hours to give an aminated cellulose gel.

To 5 ml of the obtained gel was added a solution prepared by dissolving 0.2 g of sodium polyacrylate having a molecular weight of $1.9 \times 10^5$ to $5 \times 10^5$ in 10 ml of water and adjusting the pH value to 4.5. To the mixture was added 200 mg of 1-ethyl-3 -(dimethylaminopropyl)carbodiimide while maintaining the pH value of 4.5, which was shaken at 4° C. for 24 hours. After completing the reaction, the gel was filtered off from the reaction mixture and washed with water to give a cellulose gel with immobilized polyacrylic acid. The amount of the introduced anionic functional group derived from the immobilized polyacrylic acid was 14 $\mu$mol to 1 ml of the adsorbent.

EXAMPLE 7

Cellulose gels with immobilized sodium dextran sulfate were obtained in the same manner as in Preparation Example 1 and Example 3 except that, instead of CK gel A3, CK gel A22 (a commercially available cross-linked porous cellulose gel made by Chisso Corporation, exclusion limit of globular proteins: $3 \times 10^7$, particle size: 45 to 105 $\mu$m), Cellulofine GCL-2000m (a commercially available cross-linked porous cellulose gel made by Chisso Corporation, exclusion limit of globular proteins $3 \times 10^6$, particle size: 45 to 105 $\mu$m), Cellulofine GCL-1000m (a commercially available porous cellulose gel made by Chisso Corporation, exclusion limit of glubular proteins: $6 \times 10^5$, particle size: 44 to 105 $\mu$m), Cellulofine GC-700m (a commercially available porous cellulose gel made by Chisso Corporation, exclution limit of globular proteins: $4 \times 10^5$, particle size: 45 to 105 $\mu$m), Cellulofine GC-200m (a commercially available porous cellulose gel made by Chisso Corporation, exclusion limit of globular proteins: $1.2 \times 10^5$, particle size: 45 to 105 $\mu$m) and Cellulofine GCL-90 (a commercially available porous cellulose gel made by Chisso Corporation, exclusion limit of globular proteins: $3.5 \times 10^4$, particle size: 45 to 105 $\mu$m) were used respectively. The amounts of the introduced anionic functional group derived from the immobilized dextran sulfate were 16, 18, 30, 24, 30 and 37 $\mu$mol to 1 ml of the adsorbent, respectively.

PREPARATION EXAMPLE 5

To 25 ml of CK gel A22 were added 10 ml of water and 30 ml of 2M NaOH, and the mixture was shaken at 40° C. for 20 minutes. Further, 12 ml of epichlorohydrine was added thereto and the mixture was shaken at 40° C. for 3 hours. After the reaction was completed, the gel was filtered off from the reaction mixture and washed with water to give an epoxidated gel.

PREPARATION EXAMPLE 6

The procedure of Preparation Example 5 was repeated except that 25 ml of a porous cellulose gel (CK gel A32 made by Chisso Corporation, exclusion limit of globular proteins: $2 \times 10^7$, particle size: 53 to 125 $\mu$m), 15 ml of water, 21 ml of 2M NaOH and 7.1 ml of epichlorohydrine were used to give an epoxidated gel.

PREPARATION EXAMPLE 7

The procedure of Preparation Example 5 was repeated except that 25 ml of a porous cellulose gel (Cellulofine GCL-2000m made by Chisso Corporation, exclusion limit of globular proteins: $3 \times 10^6$, particle size: 45 to 105 $\mu$m), 25 ml of water, 15 ml of 2M NaOH and 5 ml of epichlorohydrine were used to give an epoxidated gel.

PREPARATION EXAMPLE 8

The procedure of Preparation Example 5 was repeated except that 25 ml of a porous cellulose gel (Cellulofine GCL-1000m made by Chisso Corporation, exclusion limit of globular proteins: $6 \times 10^5$, particle size: 44 to 105 μm), 25 ml of water, 11.75 ml of 2M NaOH and 4 ml of epichlorohydrine were used to give an epoxidated gel.

PREPARATION EXAMPLE 9

The procedure of Preparation Example 5 was repeated except that 25 ml of a porous cellulose gel (Cellulofine GC-700m made by Chisso Corporation, exclusion limit of globular proteins $4 \times 10^5$, particle size: 45 to 105 μm), 25 ml of water, 8.75 ml of 2M NaOH and 3 ml of epichlorohydrin were used to give an epoxidated gel.

PREPARATION EXAMPLE 10

The procedure of Preparation Example 5 was repeated except that 25 ml of a porous cellulose gel Cellulofine GC-200m made by Chisso Corporation, exclusion limit of globular proteins $1.2 \times 10^5$, particle size: 45 to 105 μm), 25 ml of water, 7 ml of 2M NaOH and 2.5 ml of epichlorohydrin were added to give an epoxidated gel.

EXAMPLE 7a

There were prepared a solution with the total volume of 33 ml by adding 10 g of the sodium dextran sulfate used in Example 3a and water to 20 ml of the epoxidated gel (CK gel A22) obtained in Preparation Example 5. 2M NaOH was added to the solution to adjust the pH value to 10.0 and the solution was allowed to stand at 45° C. for 17 hours. After the reaction was completed, the gel was filtered off from the reaction solution and washed with water. The unreacted epoxy group in the gel was blocked by adding 0.5% aqueous solution of monoethanolamine to the gel and allowing to stand at room temperature for 20 hours. After the reaction was completed, the gel was filtered off from the reaction mixture and washed with water to give a cellulose gel with immobilized sodium dextran sulfate. The amount of the introduced anionic functional group derived from the immobilized dextran sulfate was 31 μmol to 1 ml of the adsorbent.

EXAMPLE 7b

The procedure of Example 7a was repeated except that a solution with the total volume of 36 ml was prepared by adding 10 g of the sodium dextran sulfate used in Example 3a and water to 20 ml of the epoxidated gel (CK gel A32) obtained in Preparation Example 6, and that the pH value of the solution was adjusted to 9.9 to give a cellulose gel with immobilized sodium dextran sulfate. The amount of the introduced anionic functional group derived from the immobilized dextran sulfate was 27 μmol to 1 ml of the adsorbent.

EXAMPLE 7c

The procedure of Example 7a was repeated except that a solution with the total volume of 35 ml was prepared by adding 9.3 g of the sodium dextran sulfate used in Example 3a and water to 20 ml of the epoxidated gel (Cellulofine GCL-2000m) obtained in Preparation Example 7, and that the pH value of the solution was adjusted to 9.3 to give a cellulose gel with immobilized sodium dextran sulfate. The amount of the introduced anionic functional group derived from the immobilized dextran sulfate was 30 μmol to 1 ml of the adsorbent.

EXAMPLE 7d

The procedure of Example 7a was repeated except that a solution with the total volume of 35 ml was prepared by adding 9.3 g of the sodium dextran sulfate used in Example 3a and water to 20 ml of the epoxidated gel (Cellulofine GCL-1000m) obtained in Preparation Example 8, and that the pH value of the solution was adjusted to 9.3 to give a cellulose gel with immobilized sodium dextran sulfate. The amount of the introduced anionic functional group derived from the immobilized dextran sulfate was 30 μmol to 1 ml of the adsorbent.

EXAMPLE 7e

The procedure of Example 7a was repeated except that a solution with the total volume of 36 ml was prepared by adding 9.0 g of the sodium dextran sulfate used in Example 3a and water to 20 ml of the epoxidated gel (Cellulofine GC-700m) obtained in Preparation Example 9, and that the pH value of the solution was adjusted to 9.3 to give a cellulose gel with immobilized sodium dextran sulfate. The amount of the introduced anionic functional group derived from the immobilized dextran sulfate was 30 μmol to 1 ml of the adsorbent.

EXAMPLE 7f

The procedure of Example 7a was repeated except that a solution with the total volume of 36 ml was prepared by adding 9.0 g of the sodium dextran sulfate used in Example 3a and water to 20 ml of the epoxidated gel (Cellulofine GC-200m) obtained in Preparation Example 10, and that the pH valve of the solution was adjusted to 9.2 to give a cellulose gel with immobilized sodium dextran sulfate. The amount of the introduced anionic functional group derived from the immobilized dextran sulfate was 32 μmol to 1 ml of the adsorbent.

EXAMPLE 8

The procedures of Preparation Example 1 and Example 3 were repeated except that the epoxy-activated Sepharose CL-6B (a commercially available epoxidated cross-linked agarose gel made by Pharmacia Fine Chemicals AB, exclusion limit of globular proteins: $4 \times 10^6$, particle size: 45 to 165 μm) was used to give a gel with immobilized sodium dextran sulfate. The amount of the introduced anionic functional group derived from the immobilized dextran sulfate was 20 μmol to 1 ml of the adsorbent.

EXAMPLE 9

The procedures of Preparation Example 1 and Example 3 were repeated except that FP-HG (a commercially available hydrophilic porous hard hydrogel containing methyl polymethacrylate as a main component, made by Mitsubishi Kasei Kogyo Kabushiki Kaisha, exclusion limit of globular proteins: $4 \times 10^6$, particle size: 120 μm) to give a gel with immobilized dextran sulfate. The amount of the introduced anionic functional group derived from the immobilized dextran sulfate was 9 μmol to 1 ml of the adsorbent.

EXAMPLE 10

There was prepared an aminated cellulose gel in the same manner as in Example 6. To 2 g of the obtained gel was added a solution prepared by dissolving 4g of sodium dextran sulfate (molecular weight: 5,000, sulfur content: 15% ) in 8 ml of buffer solution of 0.1M phosphoric acid (pH 8.0) and the mixture was shaken for 16 hours at room temperature. After completing the reaction, 20 mg of NaCNBH$_3$ was added to the reaction mixture, which was stirred for 30 minutes at room temperature and heated at 40° C. for 4 hours. Then, the gel was filtered off from the reaction mixture and washed with water to give a cellulose gel with immobilized dextran sulfate. The amount of the introduced anionic functional group derived from the immobilized dextran sulfate was 18 μmol to 1 ml of the adsorbent.

EXAMPLE 11

A polypropylene minicolumn (inner diameter: 7 mm) was filled with 1 ml of each adsorbent obtained in Examples 1 to 6 and Example 10. After the adsorbent was washed with 0.15M Tris buffer (pH 7.6), 0.1 ml of serum containing an anatibody to dsDNA which was diluted ten times with 0.15M Tris buffer was passed through the column. Then, the adsorbent was further washed with 5 ml of 0.15M Tris-HCl buffer (pH 7.6). Titers of anti-dsDNA antibodies in the fraction passed through the adsorbents were measured according to enzyme linked immunosorbent assay (ELISA Method). Briefly, flat-bottomed microtiter plates were coated with dsDNA and incubated for one hour at room temperature. Following incubation, the remaining binding sites in the well were blocked by incubation with 1%BSA, and afterwards the diluted samples were added to the wells. After one hour of incubation, the plates were washed and peroxidase conjugated anti-human IgG were then added to the wells and incubated. After washing again, substrate solution was added to the wells. The color reaction was stopped by addition of H$_2$SO$_4$, and absorbance valves at 486 nm were read on an automatic ELISA reader (SLT210, Labo-Science, Japan).

The compounds with immobilized anionic functional groups as shown in Table 1 with the values of antibody titer of the adsorbent. Each antibody titer of the adsorbent is shown as a relative antibody titer calculated as follows:

Relative antibody titer (%) =

$$\frac{\text{Titer of anti-dsDNA antibody in the fraction passed through the adsorbents}}{\text{Titer of anti-dsDNA antibody in the original serum}} \times 100$$

TABLE 1

| Ex. No. | Compound having the anionic functional group | Relative antibody titer (%) |
|---|---|---|
| 1 | Sulfanilic acid | 32.6 |
| 2 | Phosphoryl ethanolamine | 58.9 |
| 4 | Glycine | 50.0 |
| 5 | Taurine | 61.8 |
| 6 | Polyacrylic acid | 5.7 |
| 3 | Sodium dextran sulfate | 3.4 |
| 10 | Sodium dextran sulfate | 0.2 |

From the results shown in Table 1, it is confirmed that the adsorbent with immobilized polyacrylic acid or sodium dextran sulfate has an excellent capacity for adsorbing the anti-dsDNA antibody.

EXAMPLE 12

A polypropylene minicolumn (inner diameter: 7 mm) was filled with 1 ml of each adsorbent obtained in Examples 1 to 6 and Example 10. After the adsorbent was washed with 0.15M Tris-Hcl buffer (pH 7.4), 0.1 ml of serum containing an rheumatoid factor composed of IgM (hereinafter referred to as "IgM RF") which was diluted ten times with 0.15M Tris-HCl buffer was passed through the column. The, the adsorbent was further washed with 5 ml of 0.15M Tris-HCl buffer (pH 7.6). The titer of IgM RF of the fraction passed through the adsorbents was measured according to ELISA Method. Briefly, wells of a microtiter plates were coated with rabbit IgG and incubated for two hours at room temperature. Following incubation, the remaining binding sites in the well were blocked by incubation with 1%BSA, and afterwards the diluted samples were added to the wells. After one hour of incubation, the plates were washed and peroxidase conjugated anti-human IgM were then added to the wells and incubated. After washing again, substrate solution was added to the wells. The color reaction was stopped by addition of H$_2$SO$_4$, and absorbance values at 486 nm were read on an automatic ELISA reader (SLT210, Labo- Science, Japan).

The compounds with immobilized anionic functional groups are shown in Table 2 with the value of the titer of IgM RF of the adsorbent. Each titer of IgM RF of the adsorbent is shown as a relative titer of IgM RF calculated as follows:

Relative titer of IgM RF(%) =

$$\frac{\text{Titer of RF of the fraction passed through the adsorbents}}{\text{Titer of RF of the original serum}} \times 100$$

TABLE 2

| Ex. No. | Compound having the anionic functional group | Relative titer of RF (%) |
|---|---|---|
| 1 | Sulfanilic acid | 40.8 |
| 2 | Phosphoryl ethanolamine | 87.0 |
| 4 | Glycine | 99.0 |
| 5 | Taurine | 86.6 |
| 6 | Polyacrylic acid | 3.0 |
| 3 | Sodium dextran sulfate | 0.3 |
| 10 | Sodium dextran sulfate | 0.1 |

From the results shown in Table 2, it is confirmed that the adsorbent with immobilized polyacrylic acid or sodium dextran sulfate has an excellent capacity for adsorbing IgM RF.

EXAMPLE 13

The procedure of Example 11 was repeated except that the adsorbents obtained in Example 3 and Examples 7 to 9 were used to conduct the measurement of the antibody titer. The results are shown in Table 3 with the water-insoluble porous materials used in the Examples.

TABLE 3

| Ex. No. | Water-insoluble porous material | Relative antibody titer (%) |
|---|---|---|
| 3 | CK gel A3 | 3.4 |
| 7 | CK gel A22 | 1.2 |

TABLE 3-continued

| Ex. No. | Water-insoluble porous material | Relative antibody titer (%) |
|---|---|---|
| 7 | Cellulofine GCL-2000m | 4.3 |
| 7 | Cellulofine GC-700m | 42.8 |
| 7 | Cellulofine GC-200m | 65.7 |
| 7 | Cellulofine GCL-90 | 97.6 |
| 8 | Sepharose CL-6B | 5.1 |
| 9 | FP-HG | 19.4 |

From the results shown in Table 3, it is confirmed that Cellulofine GC-200 m and Cellulofine GCL-90, which are cellulose gels having an exclusion limit smaller than that of anti-DNA antibodies, i.e. about $1.6 \times 10^5$ or smaller, are inferior in the capacity for adsorbing anti-dsDNA antibodies.

EXAMPLE 14

The procedure of Example 12 was repeated except that the adsorbents obtained in Example 3 and Examples 7 to 9 were used to conduct the measurement of the titer of RF. The results are shown is Table 4 with the water-insoluble porous materials used in the Examples.

TABLE 4

| Ex. No. | Water-insoluble porous material | Relative titer of RF (%) |
|---|---|---|
| 3 | CK gel A3 | 0.3 |
| 7 | CK gel A22 | 0.2 |
| 7 | Cellulofine GCL-2000m | 0.2 |
| 7 | Cellulofine GC-700m | 35.3 |
| 7 | Cellulofine GC-200m | 74.5 |
| 7 | Cellulofine GCL-90 | 98.2 |
| 8 | Sepharose CL-6B | 9.6 |
| 9 | FP-HG | 5.1 |

From the results shown in Table 4, it is confirmed that Cellulofine GC-200 m and Cellulofine GCL-90, which are cellulose gels having a small value of the exclusion limit, are inferior in the capacity for adsorbing RF.

EXAMPLE 15

The procedure of Example 11 was repeated except that serum of the patient with SLE which contains antibodies to ssDNA was used instead of the serum containing anti-dsDNA antibodies to conduct the measurement antibody titer of anti-ssDNA antibodies. The results are shown in Table 5 with the compounds having the anionic functional group.

TABLE 5

| Ex. No. | Compound having the anionic functional group | Relative antibody titer (%) |
|---|---|---|
| 1 | Sulfanilic acid | 71.1 |
| 2 | Phosphoryl ethanolamine | 92.3 |
| 4 | Glycine | 80.8 |
| 5 | Taurine | 96.1 |
| 6 | Polyacrylic acid | 45.7 |
| 3 | Sodium dextran sulfate | 33.3 |
| 10 | Sodium dextran sulfate | 20.2 |

From the results shown in Table 5, it is confirmed that the adsorbent with immobilized polyanionic compound has an excellent capacity for adsorbing anti-ssDNA antibodies.

EXAMPLE 16

Serum of a patient in which RF were recognized was passed through a Sephadex G-200 column to separate IgM from IgG and albumin. Two ml of the obtained fraction of IgM was passed through the column in the same manner as in Example 12 and the adsorbent was washed with 1 ml of 0.15M Tris-HCl buffer (pH 7.6). Then, the relative titer of RF was measured with respect to the frction passed through the adsorbents, but IgM RF was not observed in the fraction.

From the results, it is presumed that RF is not adsorbed through a molecule of IgG, but directly adsorbed in the adsorbent.

EXAMPLE 17

After the adsorbents obtained in Examples 1a, 2a, 3a and 5a to 5i were washed with 0.5M phosphate buffer (pH 7.4), 0.1 ml of each adsorbent was put into a polypropylene microtube (capacity: 1.5 ml), and 0.5M phosphate buffer (pH 7.4) was added thereto to make the total volume 1 ml. Thereto was added 0.2 ml of serum including anti-phospholipid antibodies and the mixture was shaken at 37° C. for 2 hours. After the adsorption was conducted, the gel was precipitated by the centrifugation, and then, the antibody titer of the anti-phospholipid antibody in the obtained supernatant fluid was measured according to the ELISA method. That is, the diluted supernatant fluid was dropped on a plate coated with cardiolipin to conduct antigen-antibody reaction. Then, peroxidase conjugated anti-human immunoglobulin antibody was added thereto, and the antibody titer of the anti-phospholipid antibody was measured by observing the color reaction using CS-930 (made by Shimadzu Corporation).

The values of the antibody titer of the adsorbent are shown in Table 6 with the compounds with immobilized anionic functional groups. Each antibody titer of the anti-phospholipid antibody is shown as a relative antibody titer calculated as follows:

Relative antibody titer (%) =

$$\frac{\text{Antibody titer of the anti-phospholipid antibody in the supernatant liquid after the adsorption was conducted}}{\text{Antibody titer of the anti-phospholipid antibody in the original serum}} \times 100$$

TABLE 6

| Ex. No. | Compound having the anionic functional group | Relative antibody titer in the supernatant fluid (%) |
|---|---|---|
| 1a | Sulfanilic acid | 72.3 |
| 5a | 2-Aminoethyl hydrogensulfate | 82.2 |
| 5d | Terephthalic acid | 64.0 |
| 2a | Phosphoryl ethanolamine | 84.9 |
| 5c | Barium glucose-6-phosphate | 81.9 |
| 5b | 1,2-Ethanedithiol | 68.0 |
| 3a | Sodium dextran sulfate | 51.2 |
| 5e | Sodium dextran sulfate | 47.1 |
| 5f | Sodium dextran sulfate | 47.3 |
| 5i | Sodium dextran sulfate | 43.0 |
| 5g | Polyacrylic acid | 58.1 |
| 5h | Polyacrylic acid | 61.9 |

From the results shown in Table 6, it is confirmed that the adsorbent with immodilized dextran sulfate or polyacrylic acid has an excellent capacity for adsorbing the anti-phospholipid antibody.

EXAMPLE 18

The procedure of Example 17 was repeated except that the adsorbents obtained in Example 3a and 7a to 7f were used and that the amount of the serum added was changed to 0.15 ml, and then, the relative antibody was calculated. The results are shown in Table 7 with the water-insoluble porous materials.

TABLE 7

| Ex. No. | Water-insoluble porous material | Exclusion limit of globular proteins | Relative antibody titer in the supernatant fluid (%) |
| --- | --- | --- | --- |
| 3a | CK gel A3 | $5 \times 10^7$ | 62.9 |
| 7a | CK gel A22 | $3 \times 10^7$ | 59.5 |
| 7b | CK gel A32 | $2 \times 10^7$ | 42.5 |
| 7c | Cellulofine GCL-2000m | $3 \times 10^6$ | 59.2 |
| 7d | Cellulofine GCL-1000m | $6 \times 10^5$ | 63.8 |
| 7e | Cellulofine GC-700m | $4 \times 10^5$ | 78.9 |
| 7f | Cellulofine GC-200m | $1.2 \times 10^5$ | 80.5 |

From the results shown in Table 7, it is confirmed that the adsorbent prepared by using Cellulofine GC-700m or Cellulofine GC-200m, which is a porous material having an exclusion limit of not more than $4 \times 10^5$, is inferior in the capacity for adsorbing the anti-lipidal antibody. Also, it is found that when a porous material having a too large exclusion limit, i.e. $5 \times 10^7$ is used, the capacity for adsorbing the anti-phospholipid antibody is lowered on the contrary.

EXAMPLE 19

After the adsorbents obtained in Examples 1 to 6 and 10, and for comparison, CK gel A3 which is the carrier used in Preparation Example 1 were washed with 15 M Tris buffer (pH 7.4), 0.1 ml of each adsorbent was put into a polypropylene microtube (capacity: 7 ml), and 0.15 M Tris buffer (pH 7.4) was added thereto to make the total volume 1 ml. Thereto was added 0.2 ml of serum including immune complexes and the mixture was shaken at 25° C. for 2 hours. After the adsorption was conducted, the gel was precipitated by centrifugation, and then, the concentration of immune complexes in the obtained supernatant fluid was measured according to the ELISA method. That is, the diluted supernatant fluid was dropped on a plate coated with Clq to conduct antigen-antibody reaction. Then, peroxidase conjugated anti-human immunoglobulin antibody was dropped thereon, and the color reaction was measured by using SLT-210 with the wavelength of 486 nm. The measured values were standardized according to the standard curve made by using aggregated IgG. The results are shown in Table 8 with the compound having the anionic functional group. The concentration of immune complex in the supernatant fluid with respect to the each adsorbent are shown in terms of the concentration in the original serum in consideration of being diluted the immune complexes.

TABLE 8

| Ex. No. | Compound having the anionic functional group | Concentration of immune complex in the supernatant fluid after the adsorption was conducted (μg/ml) |
| --- | --- | --- |

TABLE 8-continued

| Ex. No. | Compound having the anionic functional group | Concentration of immune complex in the supernatant fluid after the adsorption was conducted (μg/ml) |
| --- | --- | --- |
| 1 | Sulfanilic acid | 21.4 |
| 2 | Phosphoryl ethanolamine | 21.9 |
| 4 | Glycine | 22.3 |
| 5 | Taurine | 23.2 |
| 6 | Polyacrylic acid | 27.5 |
| 3 | Sodium dextran sulfate | 21.9 |
| 10 | Sodium dextran sulfate | 16.5 |
| Pre. Ex. 1 | (CK gel A3 only) | 35.4 |

From the results shown in Table 8, the adsorbents comprising a water-insoluble porous material and a compound having an anionic functional group immobilized on the porous material have an excellent capacity for adsorbing immune complexes. Among them, the adsorbent with immobilized dextran sulfate are particularly superior in the capacity for adsorbing immune complexes.

EXAMPLE 20

The procedure of Example 19 was repeated except that the adsorbents obtained in Example 3 to 7 to 9 were used, and the amount of the serum added was changed to 0.1 ml, and then, the concentration of immune complex was calculated. The results are shown in Table 9 with the water-insoluble porous materials. For comparison, the concentration of immune complex in the initial serum was measured, as the result, the concentration was 32.2 μg/ml.

TABLE 9

| Ex. No. | Water-insoluble porous material | Concentration of immune complex in the supernatant fluid after the adsorption was conducted (μg/ml) |
| --- | --- | --- |
| 3 | CK gel A3 | 10.4 |
| 7 | CK gel A22 | 8.5 |
| 7 | Cellulofine GCL-2000m | 17.2 |
| 7 | Cellulofine GCL-1000m | 21.4 |
| 7 | Cellulofine GC-700m | 27.6 |
| 7 | Cellulofine GC-200m | 27.5 |
| 7 | Cellulofine GCL-90 | 29.6 |
| 8 | Sepharose CL-6B | 24.7 |
| 9 | FP-HG | 20.3 |

From the results shown in Table 9, the adsorbent made by using a water-insoluble porous material having a exclusion limit of not more than $4 \times 10^5$, i.e. Cellulofine GC-700 m, Cellulofine GC-200 m or cellulofine GCL-90 used in Example 7 is inferior in the capacity for adsorbing immune complexes. On the contrary, when the exclusion limit of the water-insoluble porous material is too large, i.e. $5\times10^7$, the capacity for adsorbing immune complexes of the obtained adsorbent is lowered from the result on CK gel A3 used in Example 3.

In addition to the ingredients used in the Examples, other ingredients can be used in the Examples as set forth in the specification to obtain substantially the same results.

As shown in Examples, according to the present invention, the autoantibodies or immune complexes produced by combining autoantibodies with the homologous antigen can be selectively removed from body fluid.

What we claim is:

1. A method for removing at least one of an anti-DNA antibody and an anti-phospholipid antibody from a body fluid by means of an adsorbent, which method comprises the steps of:
   a) passing the body fluid through an apparatus comprising
      i) a container having a fluid inlet and a fluid outlet;
      ii) said adsorbent, within said container, consisting essentially of a water-insoluble porous material having a protein exclusion limit is $1\times10^5$ to $6\times10^7$ and dextran sulfate and/or a sodium salt thereof immobilized onto said porous material;
      iii) at least one filter through which a fluid and components included in said fluid can pass, and through which said adsorbent cannot pass; and
   b) recovering the body fluid from which at least one of the anti-DNA antibody and the anti-phospholipid antibody has been removed.

2. The method of claim 1, wherein said autoantibody is an anti-DNA antibody.

3. The method of claim 1, wherein said antibody is a anti-phospholipid antibody.

* * * * *